(12) United States Patent
Chothani et al.

(10) Patent No.: US 8,256,267 B2
(45) Date of Patent: Sep. 4, 2012

(54) METHOD AND APPARATUS FOR DETECTION, MEASUREMENT AND CONTROL OF SULFUR-TRIOXIDE AND OTHER CONDENSABLES IN FLUE GAS

(75) Inventors: Chetan Chothani, Pittsburgh, PA (US); Charles A. Lockert, Chagrin Falls, OH (US); Bernard P. Breen, South Park, PA (US)

(73) Assignee: Breen Energy Solutions, Carnegie, PA (US)

( * ) Notice: Subject to any disclaimer, the term of this patent is extended or adjusted under 35 U.S.C. 154(b) by 474 days.

(21) Appl. No.: 12/540,010

(22) Filed: Aug. 12, 2009

(65) Prior Publication Data
US 2010/0037678 A1 Feb. 18, 2010

Related U.S. Application Data

(60) Provisional application No. 61/088,923, filed on Aug. 14, 2008.

(51) Int. Cl.
*G01N 25/00* (2006.01)
(52) U.S. Cl. ...................................... 73/25.01
(58) Field of Classification Search .................. None
See application file for complete search history.

(56) References Cited

U.S. PATENT DOCUMENTS

| | | | |
|---|---|---|---|
| 4,272,986 A * | 6/1981 | Lowry et al. ................ | 73/73 |
| 5,458,010 A | 10/1995 | Traina et al. | |
| 5,567,226 A * | 10/1996 | Lookman et al. ............ | 96/74 |
| 6,677,765 B2 | 1/2004 | Breen et al. | |
| 2003/0184320 A1 | 10/2003 | Breen | |

OTHER PUBLICATIONS

European Search Report for Application No. EP 09 01 0525 dated Feb. 11, 2011.

* cited by examiner

*Primary Examiner* — Peter Macchiarolo
*Assistant Examiner* — Alex Devito
(74) *Attorney, Agent, or Firm* — Buchanan Ingersoll & Rooney PC

(57) ABSTRACT

In a method of determining amounts of condensable species present in a gas containing condensable species a probe is placed into a gas containing condensable species. The probe has a plurality of spaced apart contacts on an outer non-conductive surface. That surface is heated at a selected heating rate and then cooled at a selected cooling rate over a selected time period. During that time period current flow between the contacts and the temperature of the non-conductive surface is monitored over the selected time period. Peaks in a plot of the current flow over the selected time period and the temperature for the time corresponding to each peak are then correlated to the condensable species has a kinetic dew point at each identified temperature. The identified temperature for each identified species is compared to a predetermined correlation of dew point temperature and concentration for that species to determine the concentration of that condensable species present in the gas.

18 Claims, 14 Drawing Sheets

METHOD AND APPARATUS FOR DETECTION, MEASUREMENT AND CONTROL OF SULFUR-TRIOXIDE AND OTHER CONDENSABLES IN FLUE GAS

CROSS REFERENCE TO RELATED APPLICATION

Applicants claim the benefit under 35 U.S.C. §119(e) of pending U.S. Provisional Patent Application Ser. No. 61/088,923, filed Aug. 14, 2008.

FIELD OF THE INVENTION

This invention relates to methods and devices used to detect, measure and control pollutants such as SOx in flue gas emitted from fossil fuel burning furnaces.

BACKGROUND OF THE INVENTION

For several years the United States Environmental Protection Agency (EPA) has required operators of fossil-fueled power plants, incinerators, metal smelters, and cement kilns to monitor levels of certain gaseous species and particulates that are released into the atmosphere. These species include sulfur oxides, nitrogen oxides, carbon monoxide, carbon dioxide and oxygen which generally exit the furnace through duct work leading to the furnace stack or chimney. There are also laws and regulations that set emission standards and provide penalties for operators who fail to meet those standards. Operators of these facilities must monitor emissions and often will add materials to the flue gas to reduce the level of emissions of the certain gaseous species. Typically, monitoring is done through the insertion of a probe capable of in-situ monitoring or by an extraction probe or sampling line into the flue gas at selected locations in the furnace. In order to analyze an extracted sample for its gaseous constituents, it is sometimes necessary to remove the particulates and transport the sample to a remote location suitable for the operation of gas analysis instrumentation.

The art has developed a variety of probes that are used to take samples of flue gas from a stack. Examples of these sampling systems are disclosed in U.S. Pat. No. 5,458,010. In a traditional extractive system a pump draws gas through heated probe from a gas stream moving within stack. The sample is then transported to a remote location through a heat-traced sample line for analysis. The probe and sample line are heated to about 250° F. to prevent condensation of the moisture or acid in the sample. Next, the sample is drawn through a "chiller" which lowers the sample temperature to approximately 35° F. The water vapor thus condenses and is drained away. The sample, now dry, is then reheated and transported through an analyzer which measures the constituents of interest.

A second general type of prior art sampling system uses a dilution probe. In this design, the rate of stack sample extraction is considerably smaller than is the case with the traditional system. Here, gas is drawn through a fine filter into a device known as a "sonic orifice" or "critical-flow orifice." The sonic orifice is so called because it meters a constant volumetric flow provided that a substantial vacuum exists behind the orifice. Vacuum on the back side of the orifice is maintained by a venturi which is driven by a compressed air source. The venturi also serves to provide clean, dry dilution air which lowers the sample dew-point. The entire venturi/orifice assembly is constructed within a non-heated probe such that the dilution is accomplished at essentially stack temperature. The diluted sample is then sent to analyzer at approximately atmospheric pressure.

Temperature sensors are often provided in the probes used in the prior art sampling systems.

To control emission operators of fossil fuel burning furnaces may add ammonia, calcium, sodium compounds or other materials to the flue gas to induce the unwanted gaseous species to react with the additive and form acceptable gases or particulates that can be removed. Another technique called Selective Catalytic NOx Reduction ("SCR") uses a catalyst to control NOx emissions. Bag houses, precipitators and even filters have been used to remove particulates from the flue gas.

Whether the use of a particular additive will be successful depends not only on the composition of the flue gas, but also the temperature of the flue gas when the additive is injected. Many materials work well only within certain temperature ranges. If that material is added while the flue gas is not within the required temperature range or if too much or too little additive is injected reactions can occur that produce undesirable compounds. These compounds can foul the precipitators, reduce the efficiency of heat exchangers and create other problems.

Ammonia ($NH_3$) is in common use today as a reactant for the removal of nitrogen oxides from gas streams. But the $NH_3$ also reacts with sulfur trioxide ($SO_3$) to form ammonium sulfate (($NH_4)_2$ $SO_4$) or ammonium bisulfate (($NH_4)HSO_4$ They both can plug catalytic passages of the SCR or heat transfer devices especially the regenerative air heater, which has many small passages. This plugging can restrict the flow of the air and the flue gas so severely that the boiler must be taken off-line and the air heater cleaned. The ammonium bisulfate is much the worst offender of the two as it is very sticky through much of the exhaust gas temperature range.

U.S. Pat. No. 6,677,765 discloses a method of measuring ammonia in flue gas by using a cooled probe to measure conductivity (and corrosion) caused by condensed ammonium bisulfate. This method uses a tubular probe having spaced-apart bands or patches of the same material as the probe body. The bands or patches are attached to the probe body by an electrically insulating, high temperature material. At least one thermocouple is attached to the probe. A series of cooling tubes are provided within the probe body to direct cold air to the regions near each band. One or more probes are placed in the furnace or boiler above the ammonia injection zone. When ammonium bisulfate forms on the probe it completes an electrical circuit between the probe body and the bands. Hence, the presence of ammonium bisulfate can be detected by a change in resistance between the bands and the probe body. The ammonium bisulfate will also cause corrosion of the probe. Electrochemical noise is generated during the corrosion process. A monitor connected to the probe body can detect any change in resistance as well as electrochemical noise. Furthermore, a corrosion rate can be determined from the level or amount of electrochemical noise that is detected.

Information obtained from the probe can be correlated with the position of the probe to identify those injectors that may be the source of the detected excess ammonia. Then the injectors can be adjusted to reduce or eliminate excess ammonia injection. During the combustion of hydrocarbon fuel in air, the oxygen in the air combines with the carbon and hydrogen in the fuel to form water and carbon dioxide. In the case of combustion of methane or natural gas, the flue-gas product is a combination of a relatively clean mixture of nitrogen and excess oxygen from the air with about 10 to 12% water and 12% carbon dioxide products of combustion.

However, in the case of coal combustion there are numerous impurities such as the most voluminous being chlorine, sulfur, fuel-bound nitrogenous compounds and ash mixed with the carbon and hydrocarbons making up the coal fuel. The products of combustion are about 6% water, 12% carbon dioxide, but now there are numerous other contaminants. The ash itself contains numerous compounds which may be metals such as sodium, calcium, magnesium, silica, alumina, iron and pyretic sulfur along with many trace elements which are considered pollutants such as mercury, lead, cadmium, arsenic and numerous others. All of these species have the opportunity to vaporize and oxidize throughout the high temperature combustion environment, with the resulting coal-fired flue-gas being much more complex than in the case of natural gas combustion.

With such complex flue-gases it has always been desirable to maintain the flue-gas temperature high enough such that water should not condense within the back passes of the boiler, breeching and chimney; because the water would cause solutions of all these myriad corrosive and ash compounds to accumulate into a messy and sticky gunk. This gunk thus fouling the flue-gas passages to such an extent that the equipment becomes inoperable. At the same time, the temperature should be as low as possible to maintain the efficiency of heat recovery from the fuel combustion. In order to maintain clean, safe and efficient power plant operation it is desirable to measure the condensation and fouling temperature characteristics of the flue-gas.

The condensation of water is greatly affected by the presence of sulfur trioxide to form sulfuric acid condensate and other more complex sulfates and sulfites. These various sulfur compounds all condense at temperatures much higher than the condensate temperature of pure water and include ammonium sulfate, ammonium-bi-sulfate and the sulfates and bi-sulfates of the different metal contaminants such as sodium (sodium bi-sulfate, sodium bi-sulfite, and sodium sulfate), magnesium, calcium and others.

Thus, while it is desirable operate at the lowest possible stack temperatures, to improve efficiency for lower carbon dioxide generation; at the same time, extensive use of scrubbers allows higher sulfur coal use. The sulfur and thus sulfur trioxide in the back-pass of the boilers has thus tended to increase. When coal sulfur increases the sulfur trioxide also increases but this has been greatly aggravated by the use of Selective Catalytic NOx Reduction (SCR) which further catalyzes the sulfur trioxide formation. The complexity is increased with use of ammonia injection for both SCR and Selective non-Catalytic Reduction of NOx (SNCR), because any ammonia-slip will react with sulfur trioxide to form ammonium-bisulfate which increases water condensation and fouling temperature. Beyond the back-end fouling problem, sulfur trioxide emissions from the stack cause plume visibility and pollution problems.

Given the problems of trying to operate the back-end passes, breeching and chimney at as low a temperature as possible, while not fouling; it has come to pass that attempts to remove the sulfur trioxide are being tested and employed. Remedial reagents injected at points A, B, C and D of the furnaces, shown in FIGS. 1 and 2, while reducing sulfur trioxide, exhibit their own complex condensation and decomposition characteristics and add to the amount of ash which can potentially foul the equipment.

In order to operate within the complexity described here it would be desirable to measure sulfur trioxide and its concentration dependent sulfuric acid condensation temperature if, when and where it exists by itself. But as described here it often occurs in combination with ammonia or remedial reagents and thus cannot be measured as sulfuric acid because it may take a different form as it condenses. For example ammonium-bi-sulfate condenses at 30 to 100° F. higher temperature than $SO_3$ and thus masks the $SO_3$ dew-point with already condensed material as the dew-point is searched for.

At temperatures above 400° F., sulfur trioxide exists in dynamic equilibrium with water and sulfuric acid molecules; while to further complicate its measurement at lower temperatures it may be adsorbed in particulate and/or aerosol form. Below 400° F. the measured dew point of sulfuric acid is the measure of total sulfur trioxide; while above that temperature the total sulfur trioxide can be calculated from the equilibrium curve. However since $SO_3$, $H_2SO_4$, and condensed phase (aerosol and particulate) can be present, it is sometimes required to convert all forms into the condensable form of sulfuric acid below 400° F. These forms can be distinguished by filtration, and heating or cooling and denitrification of the sampled flue gas.

The sulfuric acid may still condense in the range of 250° F. to 290° F. but in the presence of ammonium-bi-sulfate or sodium-bi-sulfate condensation within the flue-gas may begin at temperatures above 320° F. and even to 600° F. Thus, a standard sulfuric acid dew-point instrument will become confused by a whole range of condensation phenomena in the complex flue-gas, when attempting to measure a specific sulfuric acid dew-point. For example, when present, the sodium-bi-sulfate will condense at temperatures above 350° F.; in that case it is necessary to use a clean cold probe to measure opposing rates of condensation and evaporation as the clean probe is heated from the bottom up of the probe heating cycle.

Consequently, there is a need for a method and probe that can accurately determine the amount of sulfur trioxide and other condensables in flue gas as well as any other gas containing condensable species.

SUMMARY OF THE INVENTION

In the invention disclosed here we teach that by use of a dynamic temperature change probe and by monitoring temperature changes and current changes in material that has condensed on the probe we are able to distinguish and identify the condensation and evaporation characteristics of any and all components which are present. Using this information and a correlation between of dew point temperature and concentration for the condensable species identified we can determine the concentration of that condensable species present in the gas. This measurement can then be used to define operating temperatures, injection limits and remedial process options and their process control. This dynamic process and probe device along with known measurement and control instrumentation can be applied to identifying the condensable constituents of any gas.

When inserted into a hot combustion flue gas exhaust, our probe measures the temperature at which different concentrations of condensable gases form deposits on an otherwise non-conductive surface. Through the use of controlled rates of probe temperature change, the measured current flow associated with condensate accumulation, the measured temperature at which condensation occurs and correlations between condensation temperature and amount of condensable species present we are able to determine the identity and the concentrations of these condensables. A unique aspect of our invention is that we measure a kinetic or dynamic formation and evaporation of condensate through observing current flow associated with changing temperatures, rather than seeking an equilibrium dew point which may not exist in the complex nature of a combustion flue-gas; where many different condensable compounds may coexist. Through this kinetic approach and the algorithms we have developed, we are able to separate out both the identity and the concentration of coexisting condensables.

We provide three features which allow us to correlate the $SO_3$ or other condensable concentrations to our measurements. First, we provide a probe which can be inserted into a hot flue-gas and which can be cooled or heated at a controllable rate during continuously adjustable cooling and heating cycles. Second, we monitor different concentrations of condensates causing the formation of a conductive deposit on an otherwise non-conductive surface. The onset or formation of a deposit, the rate of deposit or evaporation and the heating to dryness depend on the rate of cooling or heating of the condensate surface as well as the kinetics of diffusion and condensation of the different condensate concentrations. We then use the temperature at which peaks occur in a plot of current activity due to the rate of condensation to identify and determine the concentration of the condensable species in the gas.

We measure the formation of deposit of condensables as we pass through a cooling cycle and then measure this continuing accumulation during a sequential heating cycle; rather than attempt to zero in on a constant temperature equilibrium dew-point for a single condensing component. When there are components which cause condensation at temperatures higher than sulfur-trioxide would condense, such as ammonium-bi-sulfate, the probe in its cooling cycle measures these as forming a condensate at the higher temperature. The cooling cycle can either begin a sequential heating cycle or continue to a preset temperature which is known to be below the lowest $SO_3$ dew-point; in which case the current trace on the following heating cycle will show the kinetic dew-point for both the $SO_3$ concentration and the ammonium-bi-sulfate concentration. However, if the probe is inserted after the air-heater has cooled the flue-gas to below the ammonium-bi-sulfate condensate temperature, say below 310° F., the lower temperature condensate is due to the concentration of $SO_3$ because the ammonium-bi-sulfate was removed by the air-heater. Gases such as water condense at even lower dew-points and also exhibit a multi-peak current condensate temperature curve.

Within a controlled temperature window and with controlled rates of cooling which we disclose here, we use the measured and controlled cooling rate, the measured condensate formation temperature and the measured conductivity on the condensate surface to correlate the presence and concentration of $SO_3$ and each of its components such as $H_2SO_4$, particulate and aerosol sulfuric acid and/or other condensables in the flue-gas. At the same time, the probe when used in higher temperature windows measures the condensation and concentration of such other condensables as ammonium-bi-sulfate and at even higher temperatures sodium-bi-sulfates, should these be present.

DESCRIPTION OF THE PREFERRED EMBODIMENTS

Figure 1:
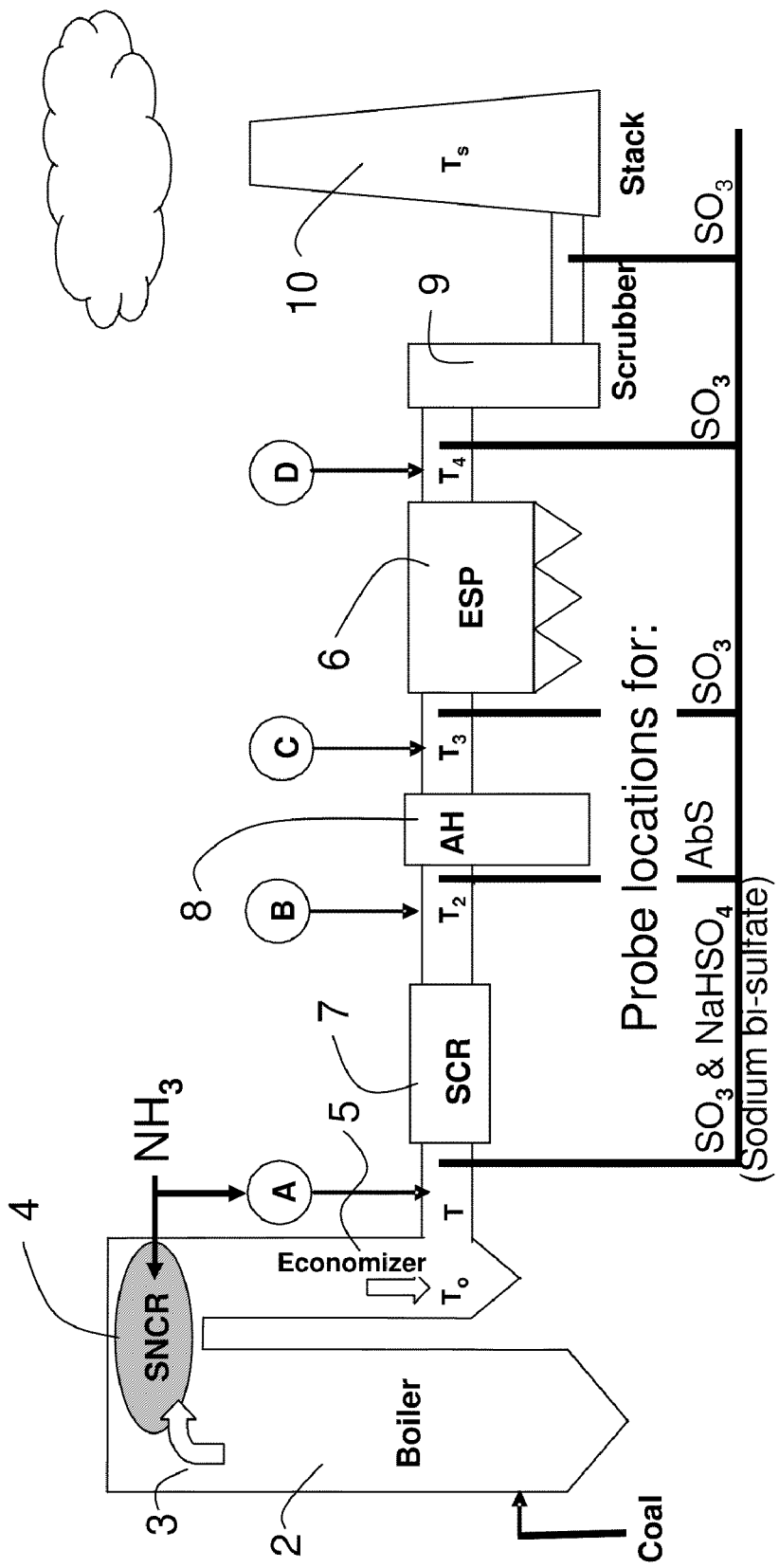
FIG. 1 is a schematic view of a coal fired boiler showing pollution and heat-recovery components with a cold-side electrostatic precipitator and reagent injection points.
Figure 2:
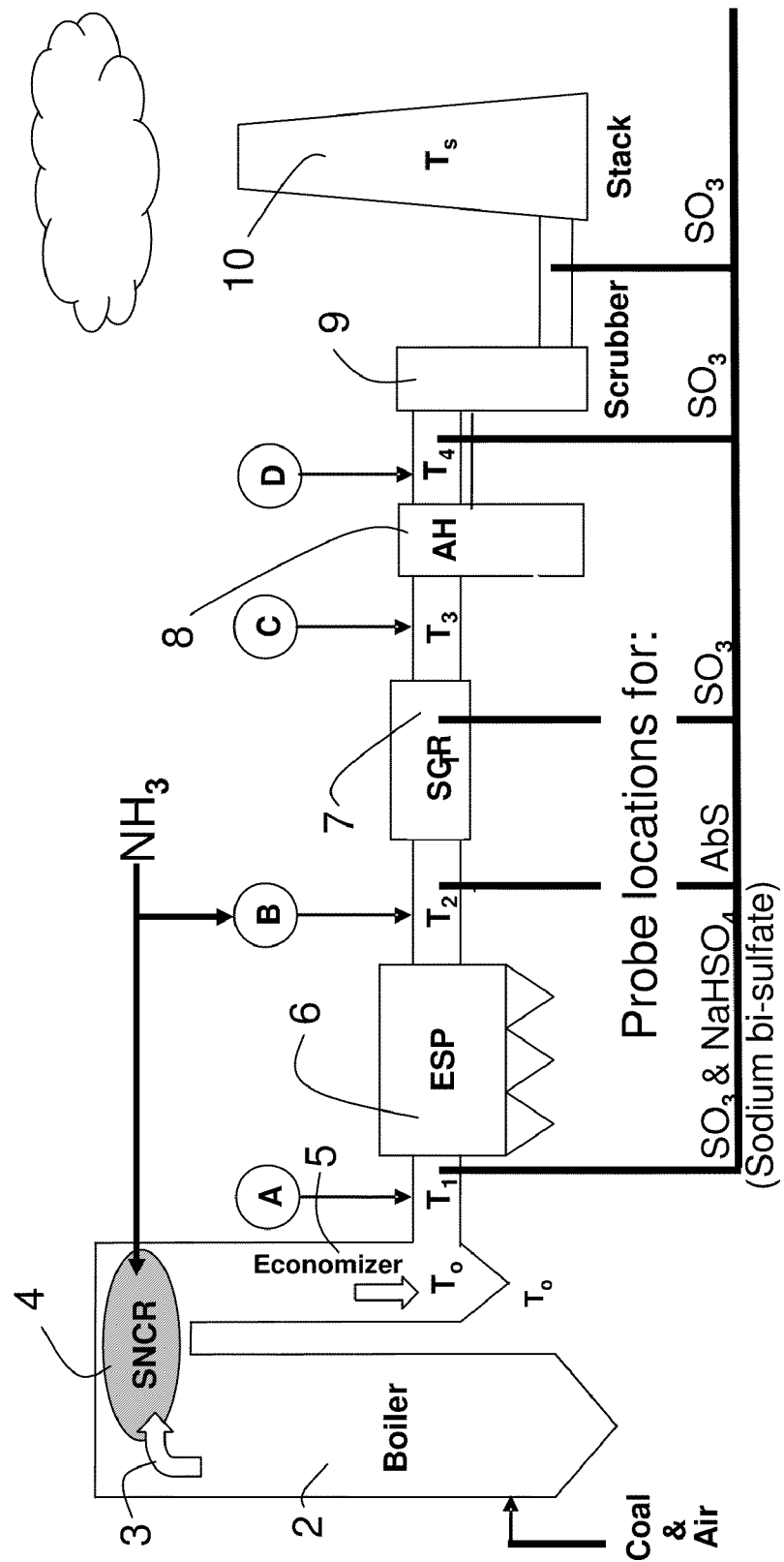
FIG. 2 is a schematic view of a coal fired boiler showing pollution and heat-recovery components with a hot-side electrostatic precipitator and reagent injection points.

In a typical coal fired furnace or boiler 2, shown in FIGS. 1 and 2, coal and air are injected into the furnace. The burning coal heats water in tubes (not shown) in the furnace wall creating steam to power a turbine. In some furnaces flue gas 3 exiting the furnace passes through a Selective non-Catalytic Reduction (SCNR) device 4. Ammonia ($NH_3$) is injected into the flue gas in the SNCR device 4 to reduce NOx in the flue gas. The flue gas then passes through an economizer 5, exiting the economizer at some temperature $T_0$. In a coal fired boiler with a cold-side electrostatic precipitator as shown in FIG. 1 the flue gas then continues through a Selective Catalytic NOx Reduction (SCR) device 7, air heater 8 and an electrostatic precipitator (ESP) 6 to scrubber 9. Then the flue gas exits the system through stack 10. In a coal fired boiler with a hot-side electrostatic precipitator shown in FIG. 2, the flue gas goes from the economizer 5 through the electrostatic precipitator 6. The flue gas continues through a Selective Catalytic NOx Reduction (SCR) device 7, air heater 8, scrubber 9 and stack 10.

FIGS. 1 and 2 provide two examples of furnaces in which our method and probe can be used, but our invention is not limited to these furnaces. Indeed, the configuration of furnaces in which our method can be used can be quite varied with NOx reduction devices such as SNCR or SCR or both present or none present and scrubbers present or not and particulate collection devices such as ESPc or ESPh or a Wet-ESP (wESP) and/or baghouse present.

Figure 3:
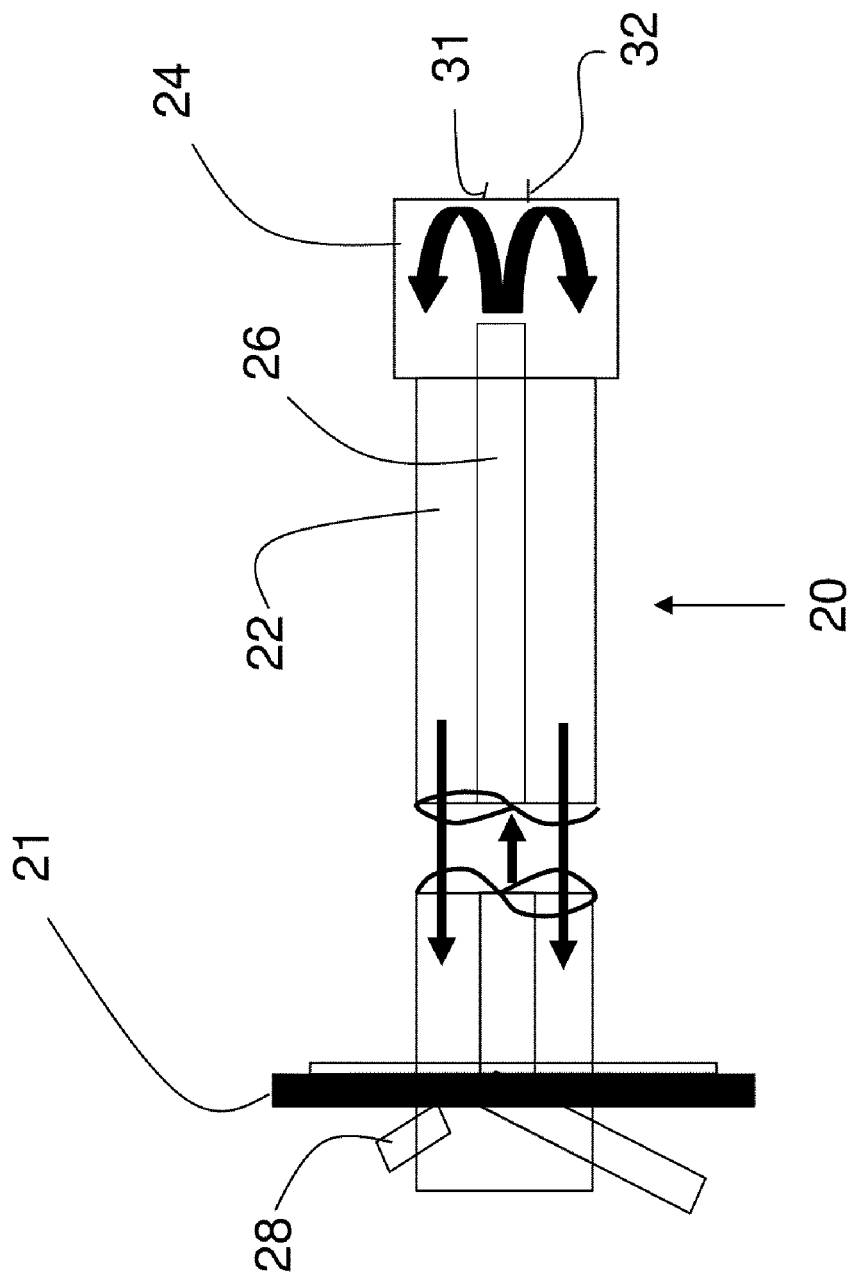
FIG. 3 is a side view of a present preferred embodiment of our probe which measures current flow through any material that has condensed on the tip surface of the probe.
Figure 4:
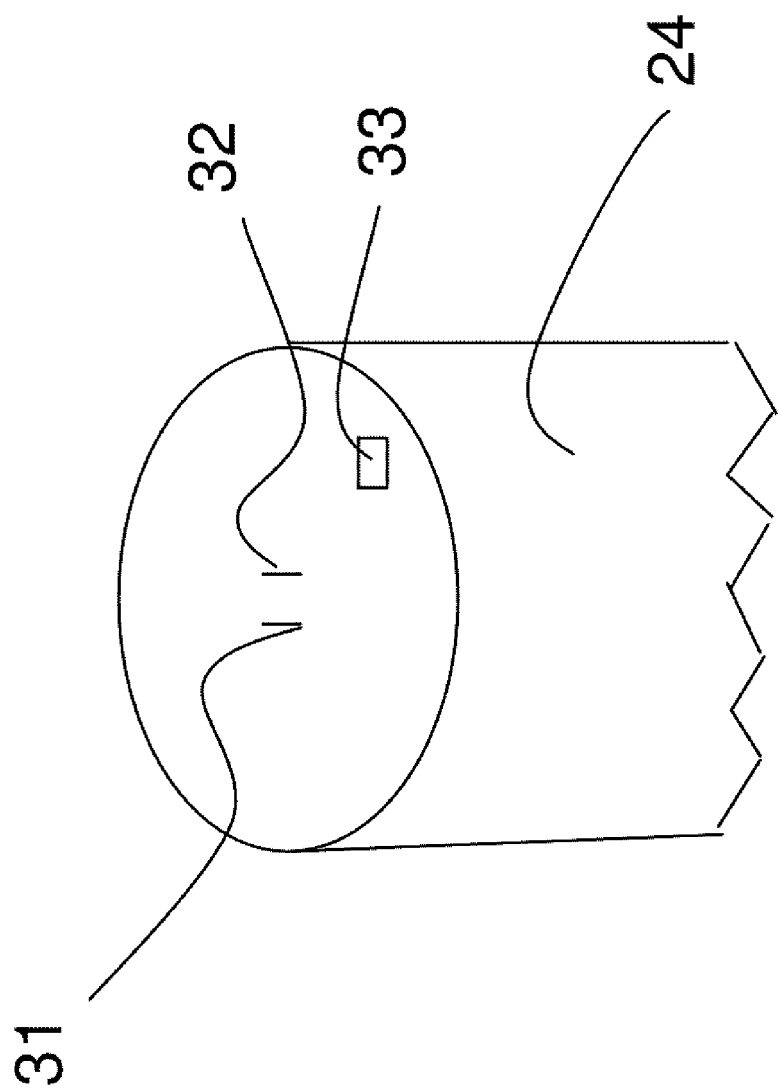
FIG. 4 is an end view of the embodiment shown in FIG. 3.
Figure 5:
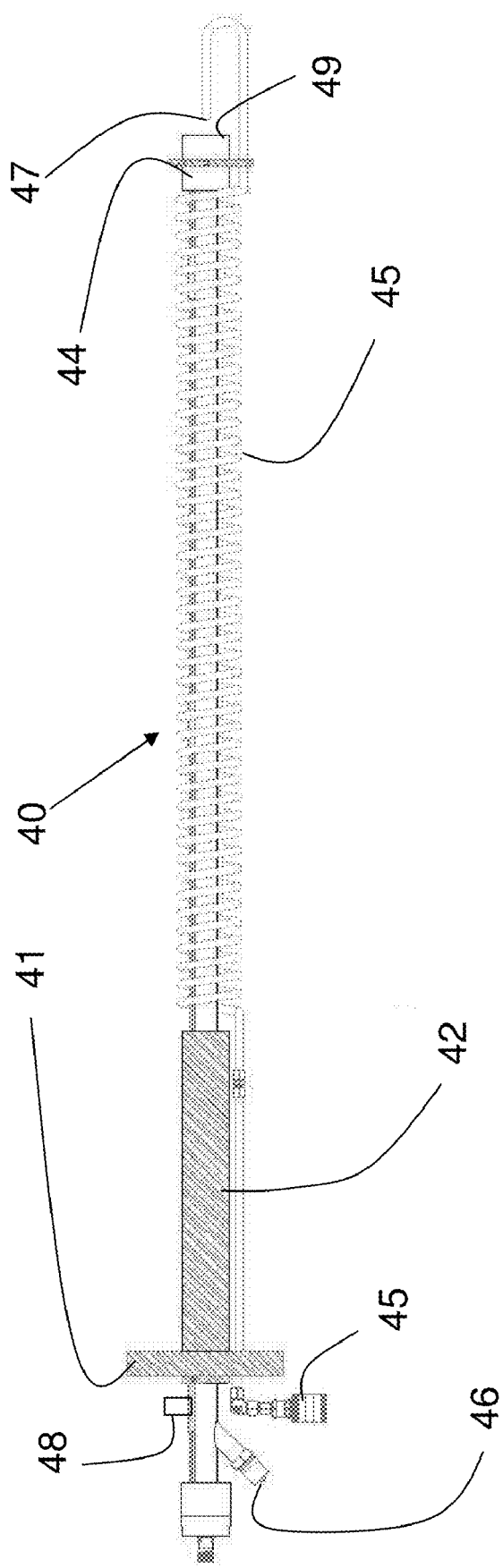
FIG. 5 is a side view of a second present preferred embodiment of our probe.

We provide a probe such as is shown in FIGS. 3, 4 and 5 which can be inserted into a hot flue-gas and cooled or heated, at a controllable rate during continuously adjustable cooling and heating cycles. The probe can be inserted into the flue gas duct at locations A, B, C and D (where the temperature is $T_1$, $T_2$, $T_3$ and $T_4$, respectively) and after the scrubber 9 as shown in FIGS. 1 and 2. The operator of the furnace may inject materials at each of locations A, B, C and D to reduce NOx or SOx. Typical injection materials are ammonia/urea (to provide $NH_3$), lime/limestone (to provide Ca), Trona (to provide Na) and magnesium oxide (to provide Mg). The different points are predicated by an interest in solving different problems. The solution to those problems depends upon knowledge or measurement and control of the effect of the reagent being added and of SO$_3$ and associated condensables.

Referring to FIGS. 3 and 4 a first preferred embodiment of our probe 20 comprises a generally cylindrical hollow body 22 which may typically be from three to six feet in length. An end cap or tip 24 is mounted on the distal end of body 22 which will be exposed to the gas stream. A cooling tube 26 is provided within and along the length of the body 22 for directing cool air to the tip 24. The flow of cool air to the tip is precisely controlled to induce condensation on the probe tip. A return air valve 28 is provided to allow the cooled air to escape after having passed over the tip. Spaced apart contacts 31 and 32 are provided on the surface of the tip 24. But, there could be more spaced apart contacts and the contacts can be variously configured and positioned in the outer surface of the tip. This surface is non-conductive. We also prefer to provide a temperature sensor 33 on the tip. Leads 33 run from the temperature sensor and contacts to the opposite end of the probe where they can be connected to monitoring equipment. When material condenses on the tip the condensate completes a circuit between the contacts. The probe is constructed of a corrosion resistant material such as a nickel chromium alloy. A mounting flange 21 is attached to the other end of body 22 and is adapted to engage mounting hardware on the duct (not shown).

A second present preferred probe 40 is shown in FIG. 5. This probe also has a generally cylindrical hollow body 42 and end cap or tip 44 is mounted on the distal end of the body 42. A cooling tube 46 is provided within and along the length of the body 42 for directing cool air to the tip 44. A return air valve 48 is provided to allow the air to escape after having passed over the tip. Spaced apart contacts and a temperature sensor (not shown) are provided on the tip. A mounting flange 41 is attached to the other end of body 42. In this embodiment we provide a heating coil 45 that winds around the cylindrical body 42 and terminates at a point near the exposed surface of the tip. This end 47 is open such that hot air passing through the heating coil will be directed against the outer surface 49 of the tip 44. The hot air will heat any condensate on the outer surface of the tip causing the condensate to become liquid or gas and flow off the tip, thereby cleaning the tip. Artificially heating the probe tip also allows operation of the probe in flue gas where the flue gas temperature is below the dew point of the condensable material such that an unheated probe would immediately get coated with condensate. This would include operating the probe in a wet stack.

Figure 6:
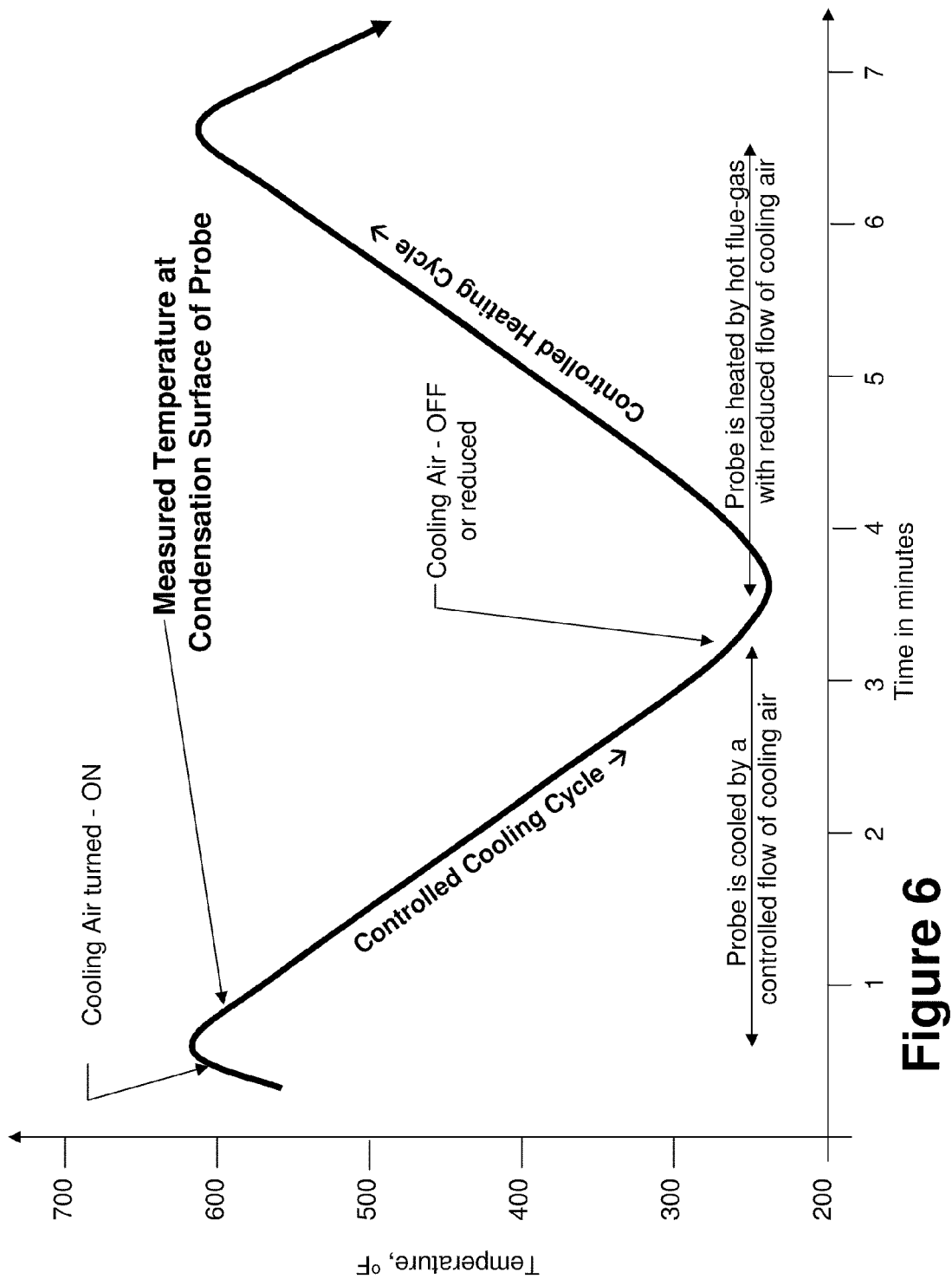
FIG. 6 is a graph showing a typical heating and cooling cycle of a probe inserted into hot flue gas and used in accordance with our method.

After the probe is inserted into a duct at a selected location, such as locations A, B, C and D in FIG. 1 or FIG. 2 the probe is cooled or heated. We provide a controlled cooling cycle and heating cycle such as is shown in FIG. 6. Each cooling/heating cycle may occur over a period of between 2 to 30 minutes usually depending on the temperature range to be surveyed which may range from 10° F. to 500° F. Control of the cooling and heating cycle is from feedback from the measured current through the surface accumulations, as shown in FIG. 7.

We monitor different concentrations of condensates causing the formation of a conductive deposit on an otherwise non-conductive surface on the tip of the probe (shown in FIG. 4). As the probe cools the onset or formation of a deposit is measured as the Formation Temperature (TFm) of that condensable and is indicated by a rise of the surface current above a set threshold current. Before this threshold current is measured the current flow, as shown in FIG. 7, was essentially zero across the hot, clean and dry surface which is being cooled.

Once a deposit has formed the cooling air is decreased or turned off and the rate of deposit or evaporation and the heating to dryness depend upon the rate of cooling or heating of the condensate surface as well as the kinetics of diffusion and condensation of the different condensate concentrations.

Figure 7:
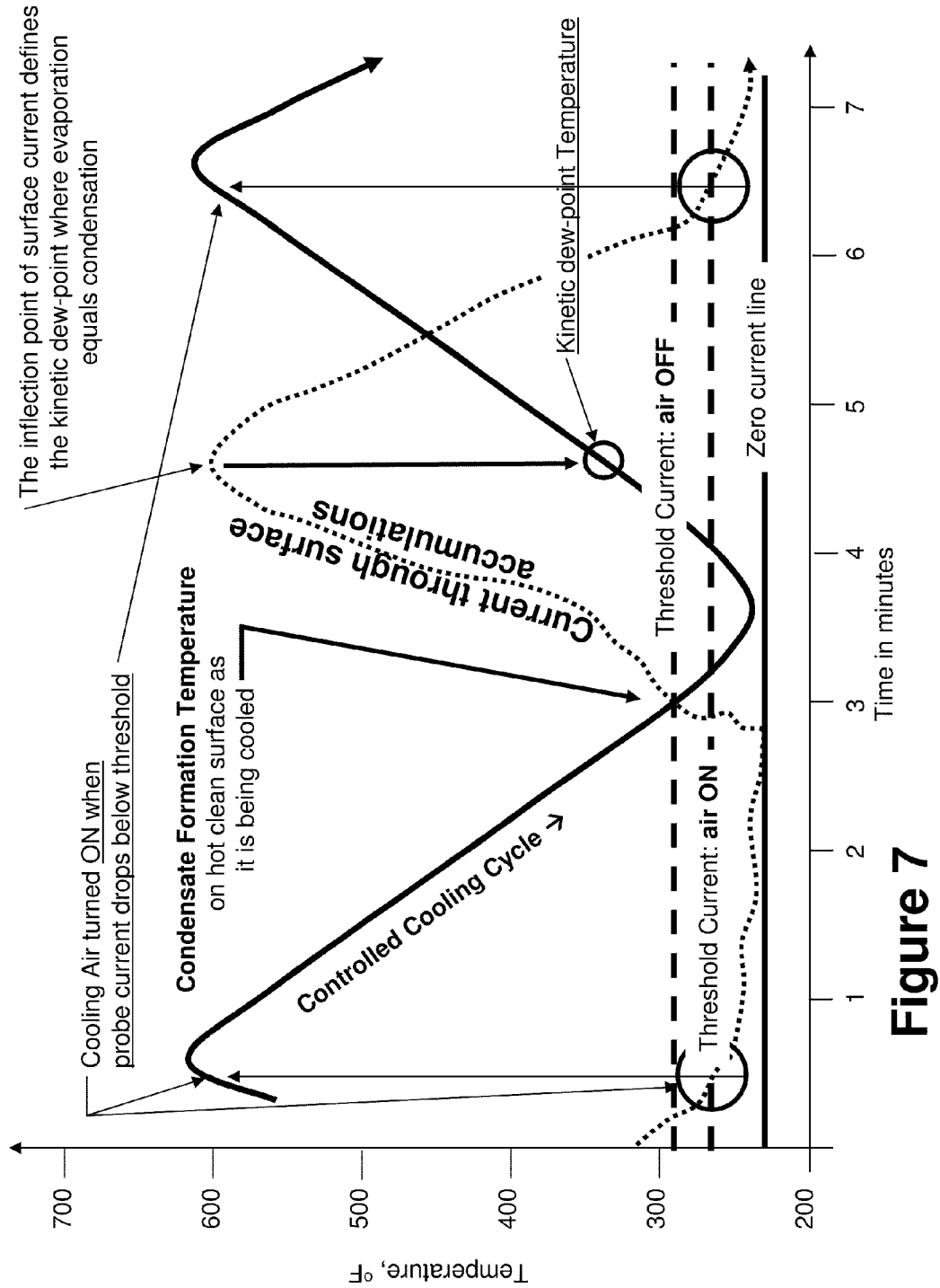
FIG. 7 is a graph similar to FIG. 6 on which current flow is shown in dotted line and a kinetic dew point is identified for the flue gas.

The deposit will continue to form with the current flow increasing until a point of inflection is reached where the deposition equals the rate of evaporation and this defines our unique Kinetic dew-point (Kdp) as shown in FIG. 7. This Kinetic dew-point is unique to the specie being condensed and its concentration is calculated from a temperature and pressure and moisture equation that reflects the curves shown in FIG. 10. For example, if the moisture content is 10% and the inflection point corresponds to a temperature of 300° F. one would find the point on the 10% moisture curve which is at 300° F. Then one finds the corresponding concentration value for that temperature on the x-axis. In this example that value would be 43 ppm SO$_3$. Moisture concentration for flue gas is usually 12%. The curve for 12% moisture would lie between the 10% moisture curve and 14% moisture curve. While the identification of SO$_3$ concentration can be done manually from the curves in FIG. 10, those skilled in the art will recognize that one could use a computer program to make the correlation. Indeed, all of the contacts and temperature sensors in the probe could be connected to a computer which would conduct the monitoring and determine the concentration of SO$_3$ present. The inflection point and thus the kinetic dew-point are not dependent on the rate of cooling or heating even though the shape of the current curve is. The peak of the current is dependent on both concentration and the kinetics of the heating/cooling rate.

Thus, we can correlate the identity and concentration of the condensate from the rate of conductivity (current) change corresponding to the rate of temperature change of the condensing surface. This same logic allows us to use the formation temperature, the inflection point and the evaporation point to control the heating cycles and to continually publish this information, in terms of condensable specie and their concentrations.

Figure 8:
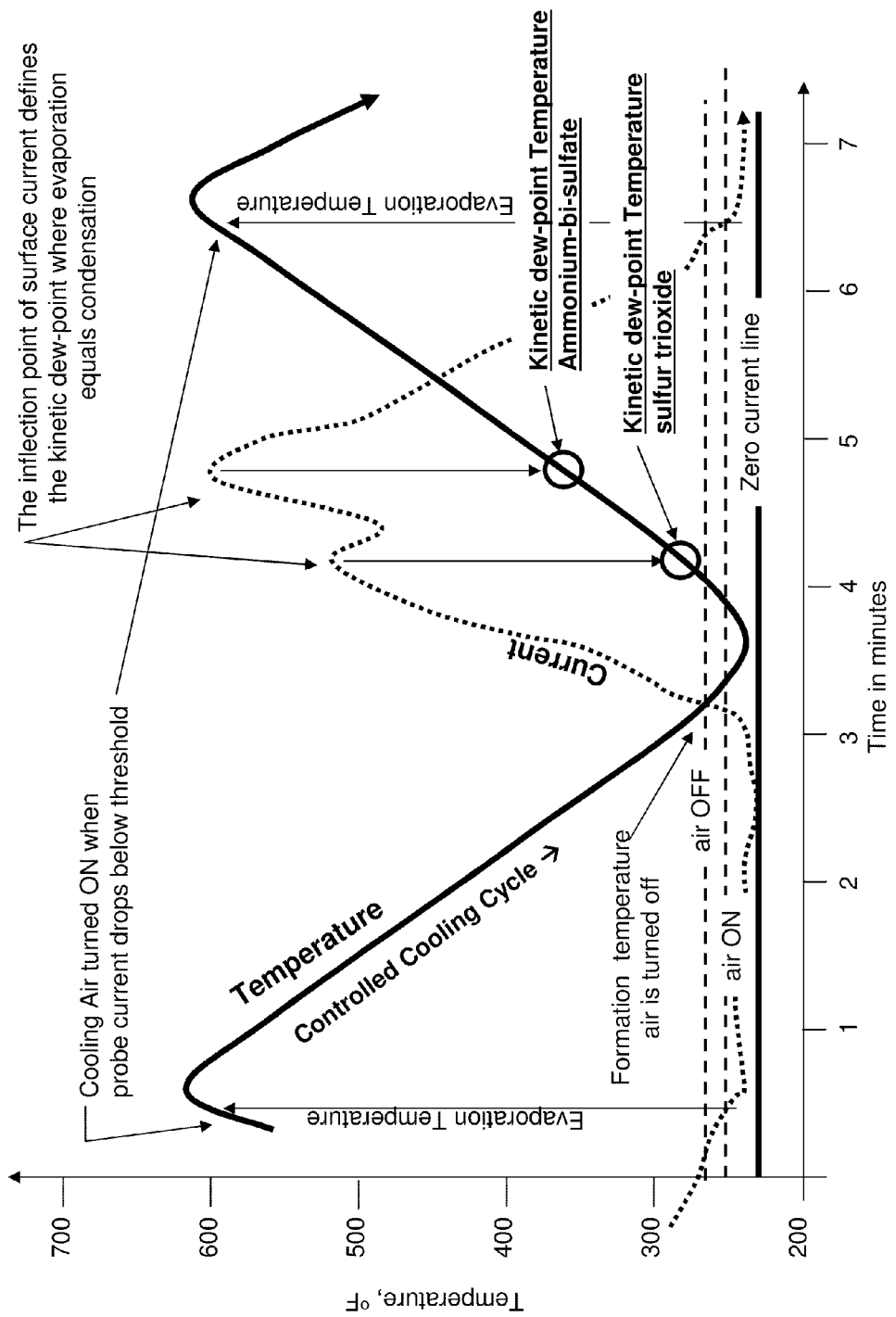
FIG. 8 is a graph similar to FIGS. 6 and 7 on which current flow is shown in dotted line and kinetic dew points for sulfur trioxide and ammonium bisulfate are identified.
Figure 9:
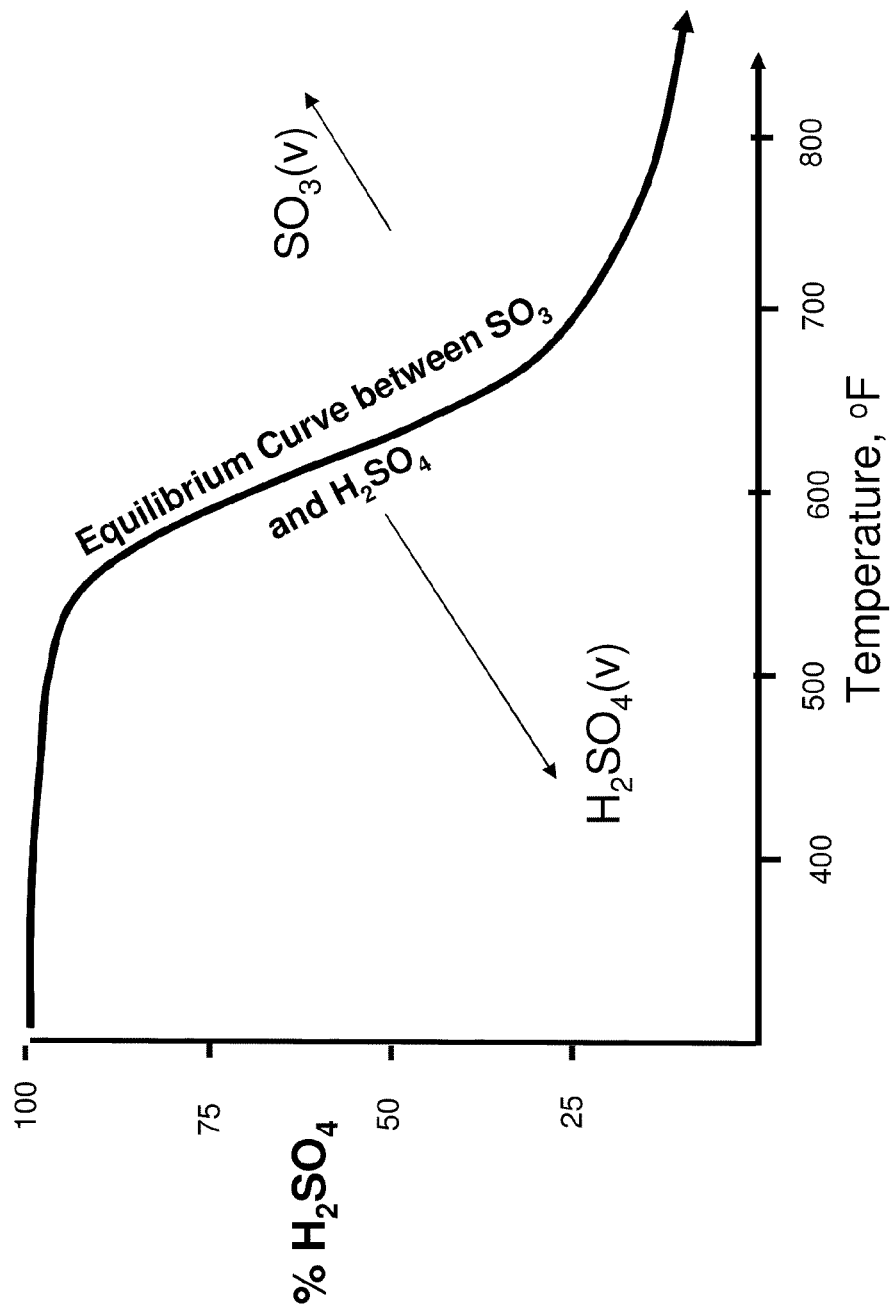
FIG. 9 is an equilibrium curve for sulfur trioxide and sulfuric acid.
Figure 10:
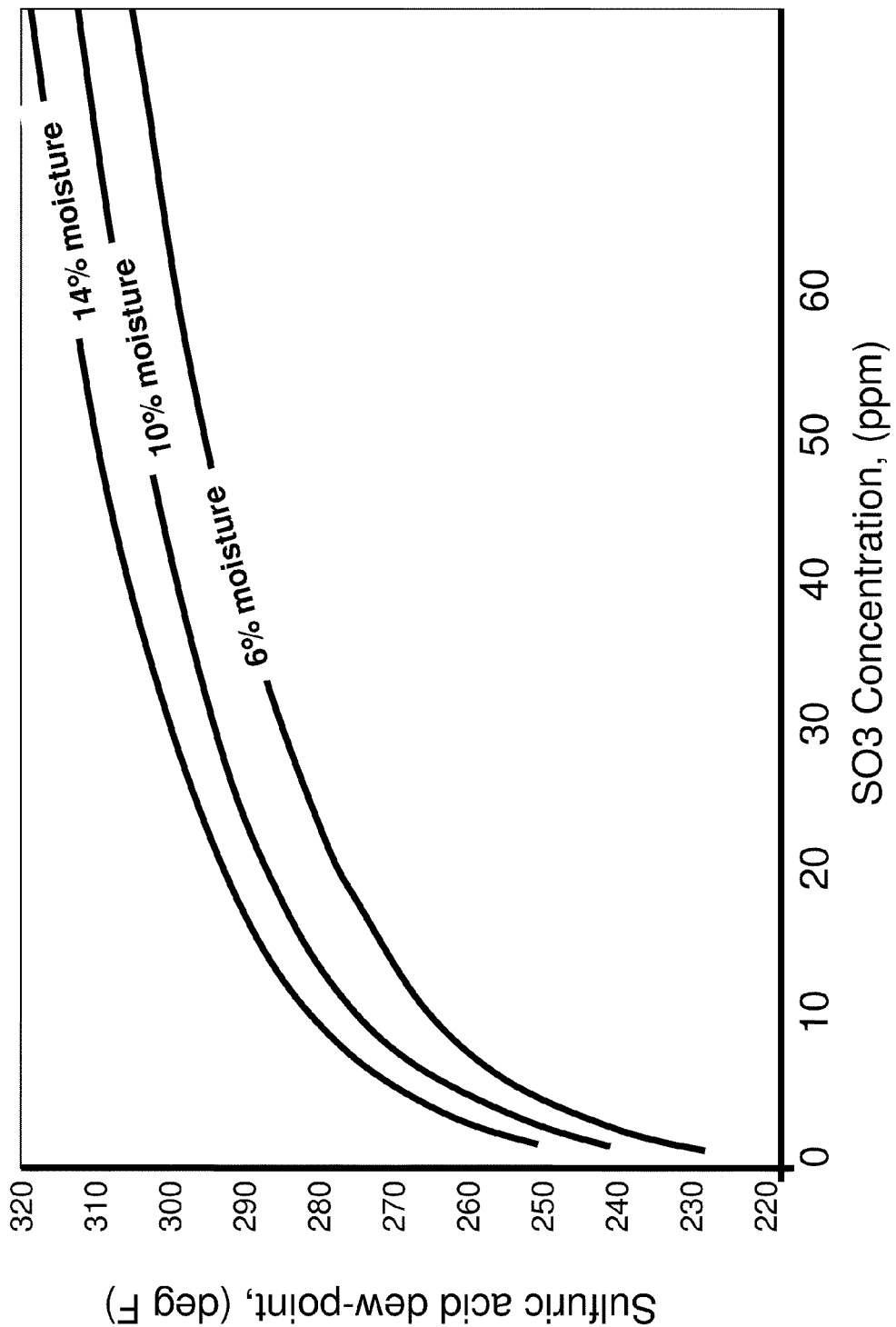
FIG. 10 is a graph showing the correlation between sulfur trioxide concentration and dew points for different concentrations of water vapor in the flue gas.
Figure 11:
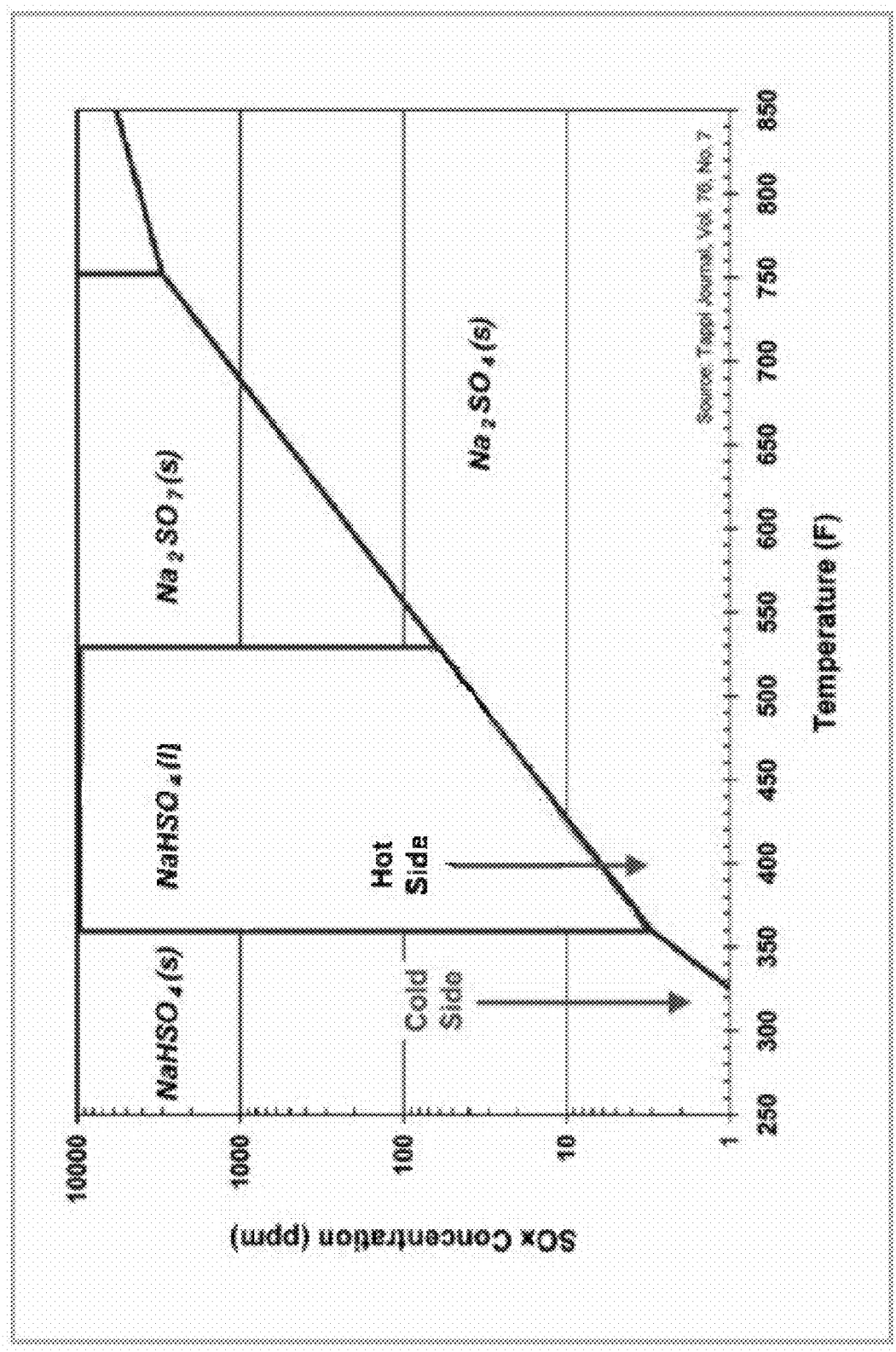
FIG. 11 is a graph showing the temperatures and concentrations at which sodium forms a liquid bisulfate.

When more than one species condenses the current curve will simply exhibit two Kinetic dew-points as shown in FIG. 8. The algorithms relating measured dew-point to SO$_3$ concentration are shown in FIGS. 10 and 11. FIG. 10 is the actual SO$_3$ concentration versus temperature while FIG. 9 shows that the dew-point is actually that of H$_2$SO$_4$ when measured at temperatures below 400° F.

The formation temperature may be determined from the top down using the cooling air to search for the SO$_3$ or other dew-point; except when a much higher temperature accumulation is known to occur, such as in the presence of injected sodium as shown in FIG. 11. In the case of sodium operation, where accumulations at temperatures of 360° F. to 530° F. are measured as shown in FIG. 11, then we will make a bottom up search for the Kinetic dew-points by quickly cooling the probe surface so as to not be covered with the higher temperature accumulation, which is solid below 350° F. In the case of sodium-bi-sulfate, as shown in FIG. 11, the SO$_3$ is measured by the algorithm controlling the cooling of the probe to quickly go below the SO$_3$ dew-point of 240 to 260° F. and then the presence of all deposits are measured from the bottom-up, including the presence of sodium-bi-sulfate.

Specific molecules have melting and boiling points where they go from solid to liquid to vapor phases. Melting and boiling points can be used to identify any substance. But in general it must be pure. For example the concentration of water in air can be determined from its dew-point temperature or its wet-bulb temperature.

Dew-point is measured as the temperature of a mirrored surface when the first droplets of moisture appear, as the surface is cooled.

Wet-bulb temperature (wb) is the temperature measured by a thermometer that is inserted within a wetted wick (or small, wet sock type covering) as air is passed over and through the wetted wick and the wick is thus cooled by evaporation to the saturation temperature of the air. The thermometer is thus cooled by evaporation of the water in the wick to the point where no more evaporation occurs because there is no temperature/vapor pressure driving force to cause the wet to evaporate into the saturated air.

Our kinetic dew-point probe measures the temperature of a mirrored surface (shown in FIG. 4) as it is heated or cooled. This probe is able to determine the temperature at which the rate of evaporation of condensed material equals the rate of condensation. This transition occurs as the condensate surface continues to be heated, the rate of evaporation becomes greater than the rate of condensation and the measured current flow begins to decrease. The temperature at this inflection or maximum in the current is the Kinetic dew point (Kdp) and it is uniquely independent of rates of heating/cooling and other physical heat and mass diffusion processes it is the molecular characteristic (vapor pressure or actual partial pressure) of the specie. This is different from maintaining a constant temperature equilibrium dew-point which is not possible in a complex multi-component flue gas with interfering condensables.

This transition point is measured by measuring the conductivity of condensed material as the probe is heated, as shown in FIG. 6. The heating cycle is initiated by first cooling the probe to a temperature where condensate formation or accumulation begins, as shown in FIG. 7, (now the probe is being heated and the measured Formation Temperature is below the species dew-point because of heat and mass diffusion kinetics) condensible material changes from accumulating with increasing current flow to depleting, after the Kinetic dew point temperature (Kdp), and thus decreasing current flow. This kinetic approach, using surface conductivity (measured as current flow), has the advantage that it can measure changes in current flow and in particular the point of inflection of the current flow as the temperature rises. This point of inflection is the actual dew-point, that is the temperature at which the rate of condensation (or deposit) from the saturated gases is equal to the rate of evaporation from the liquid surface.

In chromatography the rate of diffusion of the liquid is used to discriminate between species, now here we have disclosed a process and device which allows is to measure dew-points as a means to separate the diffusion of any component in a multi-component gas. For example, all the components of air and its pollution species can be measured by cooling to cryogenic temperatures: while, at very high temperatures the selective condensation of metals can be measured and controlled by our device.

Figure 12:
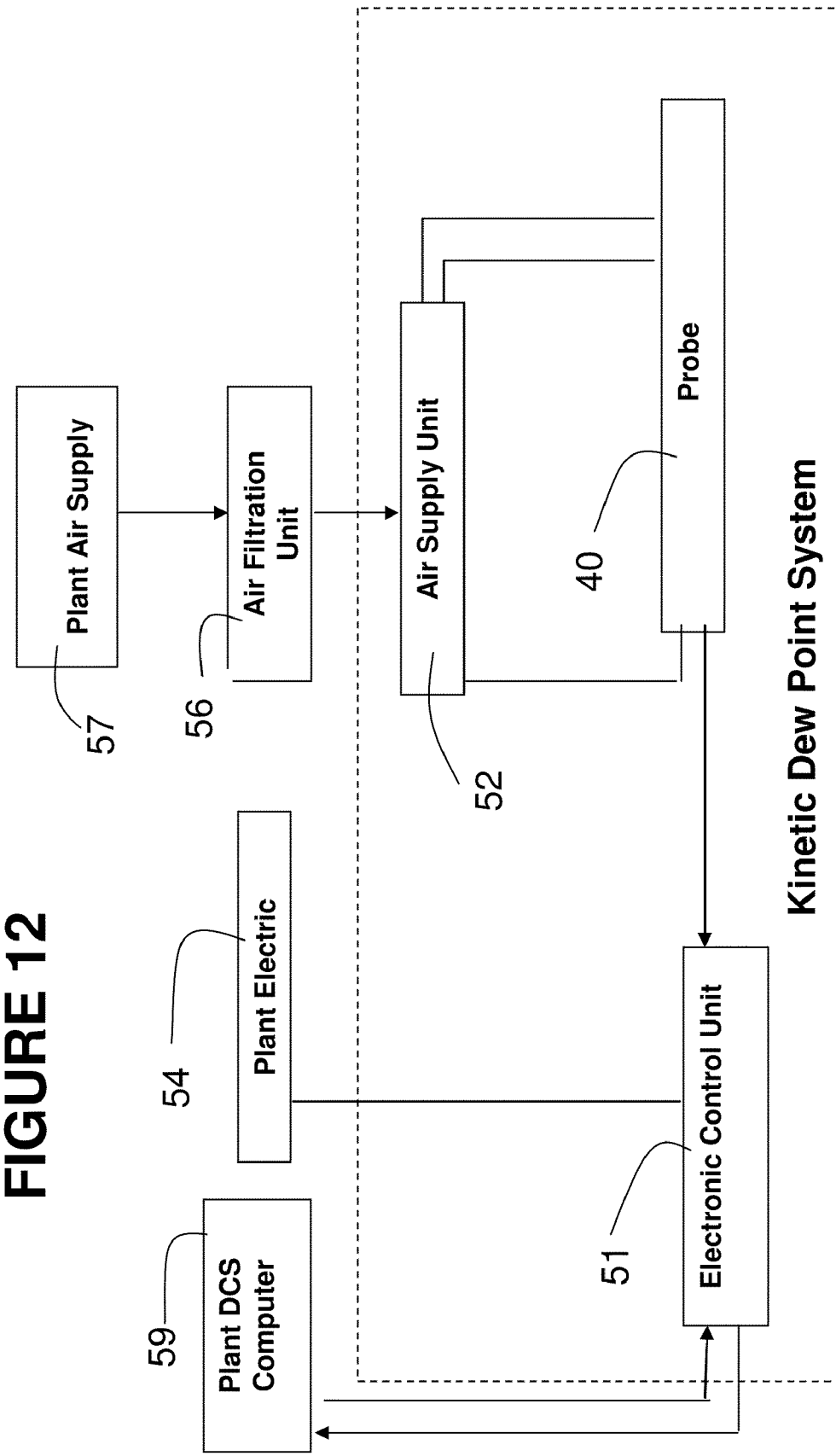
FIG. 12 is a block diagram of our kinetic dew-point system as installed in a coal burning electric power plant.

The block diagram in FIG. 12 shows our probe 40 as it would be connected to other components when using our method. An electronic control unit monitors 51 the heating and cooling of the probe and current flow. An air supply unit 52 connected to the plant air supply 57 through an air filtration unit 56 provides heated air and chilled air. The electronic control unit is also connected to the plant DCS computer 59 that controls the injection of additives into the flue gas. This unit is essentially a state-of the-art desk-top computer which is dedicated to interpreting all of the condensate/current and temperature measurements needed to control the cooling/heating cycles and to identify the presence of condensables and their concentrations. The electronic control unit receives power from the plant electrical system 54.

Figure 13:
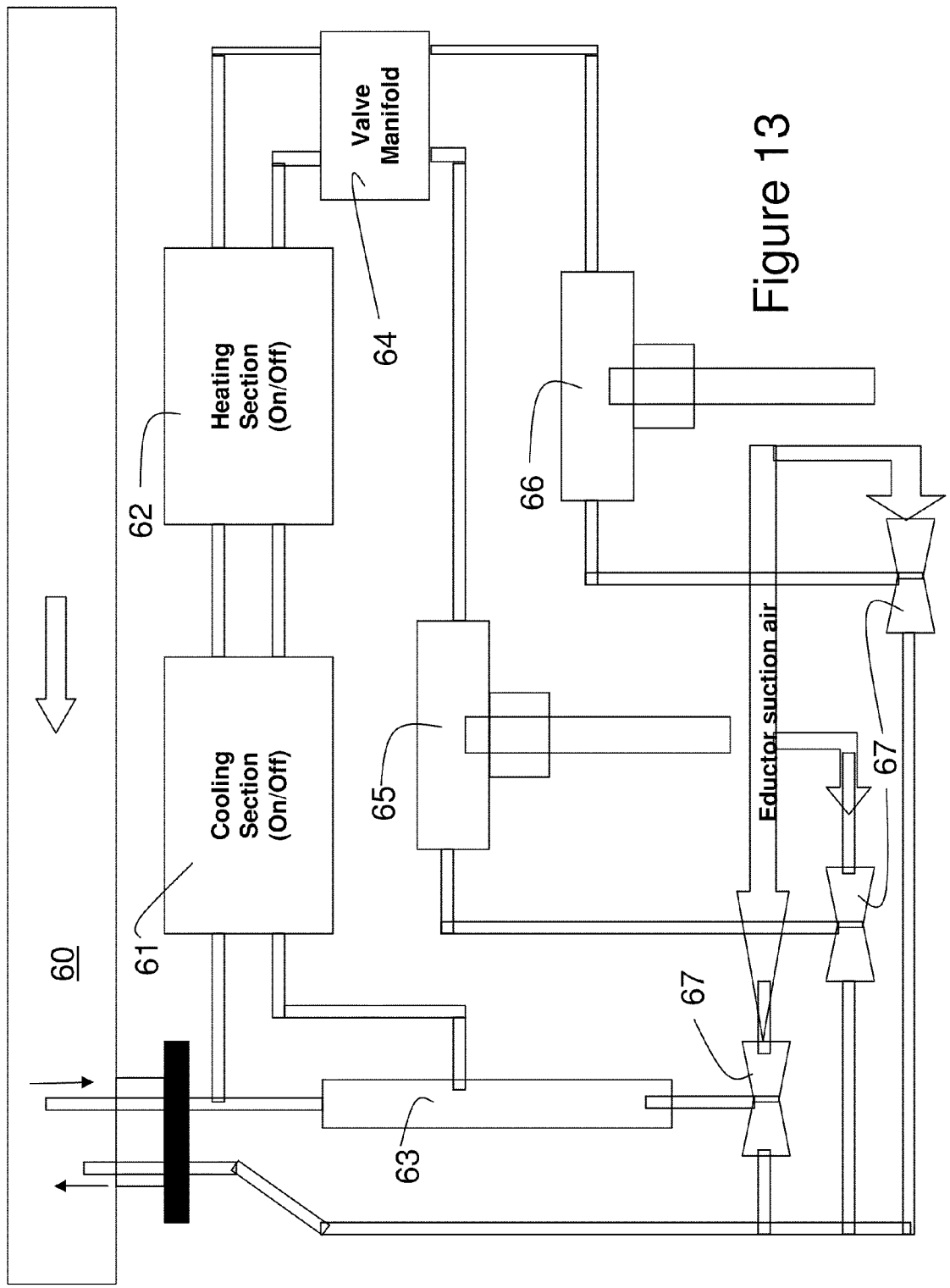
FIG. 13 is a diagram of a system that can be used for drawing a sample for a duct and conditioning the sample to separate species components.
Figure 14:
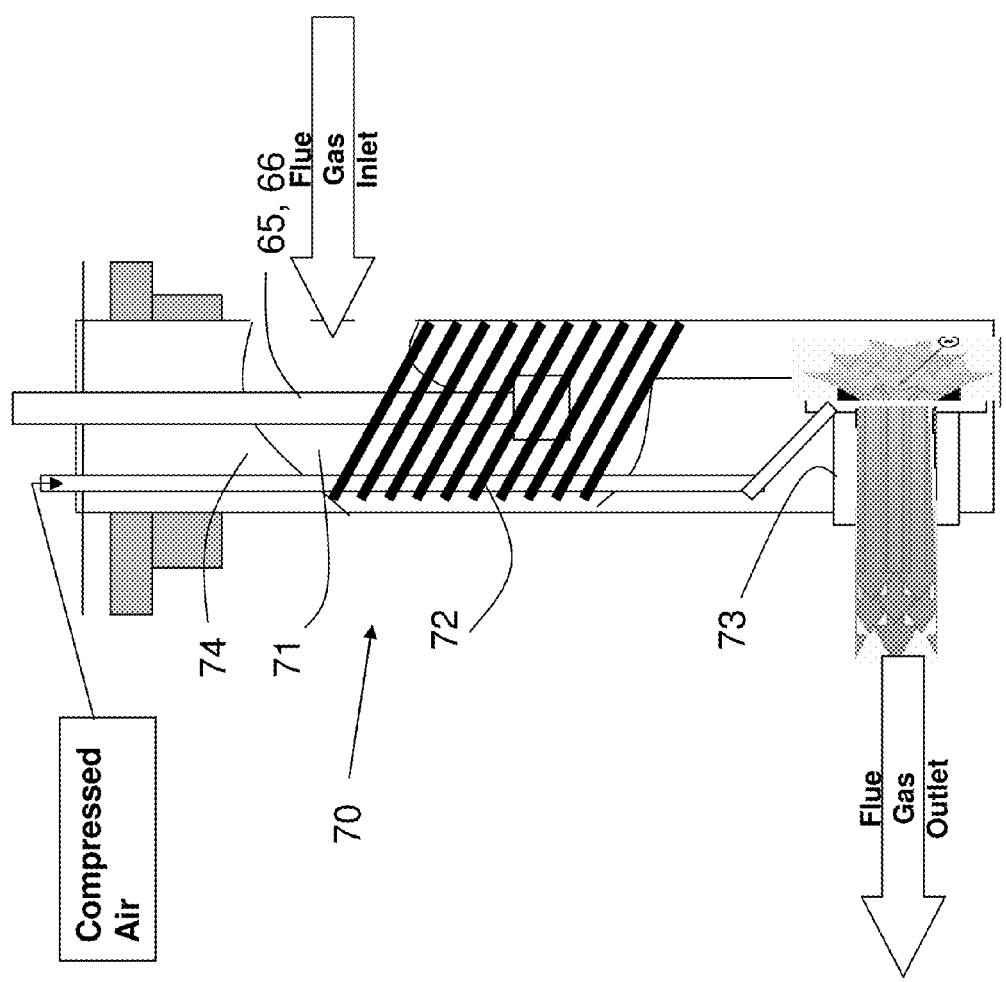
FIG. 14 is a diagram of a probe used for in-situ conditioning of flue gas in the system shown in FIG. 13.

Referring to FIG. 13 we provide a system that can be used for drawing a sample or slip stream of flue gas from a duct 60 and conditioning that sample to separate species components. The sample is drawn from the duct and directed through a chilling section 61 and a heating section 62 to either cool or heat the gas as desired. We prefer to provide an inertial filter 63 through which the gas can be passed prior to being chilled or heated. The gas which has been conditioned by heating or cooling is then directed through valve manifold 64 and past a dew-point probe 65 or 66 such as is shown in FIG. 14. Eductors 67 are provided in the system to create a suction that draws the gas sample through the system and return the gas through the duct. With this system the flue gas can be selectively heated or cooled as desired.

The system shown in FIG. 13 could be used for a slipstream of the sample with the particulate measures gaseous $H_2SO_4$ (v) and total $H_2SO_4$ and another slipstream, filtered to remove the particulate measures $H_2SO_4$ (v) and $H_2SO_4$ (aerosolized). Both of these gas streams will go through the cooling section 61 and heating section 62. Either or both of these sections may be turned off. The valve manifold 64 will allow the sample to be piped to either of the dew point monitors 65, 66 or switched after every cycle. One could multiplex the two samples to one dew point monitor.

The system shown in FIG. 13 is designed based on flow, velocity and pressure constraints to mimic the velocity in the duct (~45 ft/min) with iso-kinetic sampling. The dew point probe requires a 2" pipe connection. The system is capable of sampling in a balanced draft or positive pressure unit. The system can be used for sampling prior to the air heater (600 to 850° F.), between the air heater and ESP (400 to 300° F.), after the ESP (350 to 200° F.), in the stack (100 to 300° F.). The cooling section 61 is able to cool down flue gases from 850 down to 350° F. with temperature control. The heating section is able to heat up flue gases from 100 to 600° F. with temperature control.

In the conditioning probe 70 shown in FIG. 14 compressed air is injected to create a pressure drop that draws flue gas into the cavity 71. The pressure drop and thus the flow restriction created by such a device can be overcome by using an air amplifier 73 that uses compressed air as the motive force. A double-pilot tube (not shown) could be used to adjust the compressed air pressure to the air amplifier to ensure iso-kinetic flow. Flow director vanes 74 can be used to create the desired flow pattern across the probe tip 65, 66. The whole device could fit into a 4" flanged port.

Our method is useful for not only determining the concentration of condensables in flue gas, but also for controlling the operation of the furnace to control the rate of formation of $SO_3$ and other condensables. That control would be accomplished through the use of the plant DCS computer that controls the injection of additives into the flue gas and possibly other aspects of the furnace operation. The computer makes adjustments to the injectors or the burners based upon the presence and concentration of $SO_3$ as found with our method. Our method can provide feedback to control operating temperatures of specific plant equipment above a minimum temperature to avoid condensation and accumulation of fouling deposits. This includes controlling the SCR operating temperature above the Kinetic AbS condensation temperature to prevent catalyst fouling and controlling air heater outlet temperature to prevent condensation of fouling material in the AH and ESP.

We can use the probe feedback as an input into a thermodynamic model of a rotating air heater that calculates metal surface temperatures to determine the depth at which condensate will form (Formation Depth) as the metal temperature could be below the kinetic formation temperature and the depth beyond which the condensate will self-evaporate as the metal temperature can be greater than the kinetic evaporation temperature. Then we can examine these depths to determine if they are within the cleanable region of the air heater sootblowers and if they are beyond the cleanable region of the sootblowers, to control the air heater outlet temperature so as to increase the metal surface temperatures so that these condensation depths are within the sootblower cleanable depths. Further the probe data combined with a model of the air heater operation can be used to control the rotational speed of the air heater in real time such that the maximum metal temperature is above that necessary for self-vaporization of condensable material. We can control the maximum air heater temperature at various depths within the air heater by using various means such as heating coils, air bypass dampers and controlling the rotational speed so that the condensed material self-vaporizes. The probe provides the input into a thermodynamic model and the output of the model provides the necessary data to control this.

Our method can be used to optimize the air heater outlet temperatures so as to maximize the heat recovery (minimize the heat rate) so as to increase the efficiency of the combustion system and therefore also reduce the amount of $CO_2$ generated per unit of electricity generated.

Our probe can provide feedback to control Flue Gas Conditioning systems to ensure efficient operation of the ESP with minimized Sulphuric Acid and Sulphuric Acid Mist (SAM) at the ESP outlet so as to control Blue Plume and SAM related Opacity.

While we have discussed our method and probe in the context of a coal-fired furnace and the testing of flue gas, our method is not so limited. This method and probe extends to all condensables in any multi-component gas. This could include gasses created or found in any chemical process that involves multi-component gases as well as gases encountered in drilling oil and gas fields. Furthermore, the method can be used over a wide range of temperatures from cryogenic air through high temperature metal condensing gases.

Although we have described certain present preferred embodiments of our probe and method of determining amounts of condensable species present in a gas containing condensable species, it should be distinctly understood that the invention is not limited thereto but may be variously embodied within the scope of the following claims.

We claim:

1. A method of determining amounts of condensable species present in a gas containing condensable species comprising:
   placing a probe into a gas containing condensable species, the probe having a plurality of spaced apart contacts on a outer non-conductive surface; heating the outer non-conductive surface at a selected heating rate and then cooling the outer non-conductive surface at a selected cooling rate over a selected time period;
   monitoring current flow between the contacts over the selected time period;
   monitoring the temperature of the non-conductive surface of the probe over the selected time period;
   identifying peaks in a plot of the current flow over the selected time period;
   identifying the temperature for the time corresponding to each peak; and
   correlating which condensable species has a kinetic dew point at each identified temperature; and
   for each identified condensable species comparing the identified temperature for that species to predetermined correlation of dew point temperature and concentration for that species to determine a concentration of that condensable species present in the gas.

2. The method of claim 1 wherein the probe is heated from for a period of from ½ to 30 minutes.

3. The method of claim 1 wherein the probe is cooled from for a period of from ½ to 30 minutes.

4. The method of claim 1 wherein the gas is flue gas.

5. The method of claim 4 wherein the condensable species are at least one of ammonium bi-sulfate, sodium bi-sulfate, sulfur trioxide and water.

6. The method of claim 4 also comprising injecting into the flue gas stream an additive selected from the group consisting of ammonia, ammonia compounds, calcium, calcium compounds, sodium, sodium compounds, magnesium and magnesium compounds.

7. The method of claim 6 wherein the additive is selected based upon the condensable compounds that are identified.

8. The method of claim 4 wherein ammonia is being injected into the flue gas and ammonium bi-sulfate has been identified as the condensing compound also comprising adjusting the injection of the ammonia to minimize or eliminate ammonium bi-sulfate from the flue gas.

9. The method of claim 8 wherein the ammonia is being injected through various nozzles further comprising adjusting at least one of the nozzles to change a flow of ammonia through all of those nozzles.

10. The method of claim 1 also comprising adjusting the selected heating rate during the selected period of time.

11. The method of claim 1 also comprising adjusting the selected cooling rate during the selected period of time.

12. The method of claim 1 wherein the gas is flue gas and at least one additive is being injected into the flue gas through at least one injector comprising adjusting the at least one injector in response to the concentration of at least one condensable species that has been found in the flue gas.

13. The method of claim 1 wherein the gas is flue gas in a power generation plant and further comprising controlling operating temperatures of specific plant equipment to be above a minimum temperature to avoid condensation of a condensable species found to be present.

14. The method of claim 13 wherein the plant equipment is at least one air heater.

15. The method of claim 14 wherein the operating temperatures of the air heater are controlled to maximize heat recovery.

16. The method of claim 1 also comprising heating the probe to a temperature higher than a temperature of the gas into which the probe is inserted.

17. The method of claim 1 wherein sodium is being injected at a selected rate into the gas further comprising adjusting the rate of sodium injection after determining the concentration of a sodium compound condensable species found to be present in the gas.

18. A method of determining whether sulfur trioxide is present in a gas comprising:
   obtaining a sample of a gas that may contain sulfur trioxide;
   heating the sample to a temperature above 500° F. to decompose and vaporize all particulate and aerosol sulfuric acid present in the sample;
   cooling the sample to a temperature below 400° F. in order to convert all sulfur trioxide to sulfuric acid;
   placing a probe into the sample, the probe having a plurality of spaced apart contacts on a outer non-conductive surface; heating the outer non-conductive surface at a selected heating rate and then cooling the outer non-conductive surface at a selected cooling rate over a selected time period;

monitoring current flow between the contacts over the selected time period;

monitoring the temperature of the non-conductive surface of the probe;

determining whether there is a peak in a plot of the current flow;

identifying the temperature corresponding to each peak;

determining if an identified temperature corresponds to a kinetic dew point of sulfuric acid, passing the sample through an inertial filter which removes ash particulates after the sample has been heated and prior to cooling: and then passing the sample through a catalytic denitrification catalyst operated at a temperature in the range of 600 to 900° F.

* * * * *